United States Patent [19]
Runner

[11] Patent Number: 5,245,293
[45] Date of Patent: Sep. 14, 1993

[54] ADHESIVE BOND DEGRADATION MONITOR

[75] Inventor: Jack A. Runner, San Diego, Calif.

[73] Assignee: Teledyne Ryan Aeronautical, Division of Teledyne Industries, Inc., San Diego, Calif.

[21] Appl. No.: 811,606

[22] Filed: Dec. 23, 1991

[51] Int. Cl.⁵ ............................................. G01R 27/26
[52] U.S. Cl. ................................. 324/663; 324/693; 324/71.1; 156/64
[58] Field of Search ............... 324/693, 717, 663, 690, 324/71.1, 676, 541, 544; 156/64; 364/516

[56] References Cited

U.S. PATENT DOCUMENTS

| | | | |
|---|---|---|---|
| 2,544,673 | 3/1951 | Haber | 324/663 |
| 3,791,792 | 2/1974 | Lindsay | 324/71.1 |
| 3,803,485 | 4/1974 | Crites et al. | 324/693 |
| 4,006,063 | 2/1977 | Ensanian . | |
| 4,236,307 | 12/1980 | Colla et al. | 324/717 |
| 4,524,319 | 6/1985 | Eberling et al. | 324/693 |
| 4,553,087 | 11/1985 | Kuhn et al. . | |
| 4,581,574 | 4/1986 | Goodman et al. . | |
| 4,634,963 | 1/1987 | Lunden . | |
| 4,665,485 | 5/1987 | Lundy et al. | 364/516 |
| 4,777,431 | 10/1988 | Day et al. | 324/690 |
| 4,806,193 | 2/1989 | Von Raben et al. . | |
| 4,944,185 | 7/1990 | Clark, Jr. et al. | 324/214 |

Primary Examiner—Kenneth A. Wieder
Assistant Examiner—Glenn W. Brown
Attorney, Agent, or Firm—Brown, Martin, Haller & McClain

[57] ABSTRACT

A method and apparatus for detecting changes in the structural strength of a bonded joint. Changes in one or more dielectric properties of the bonding adhesive, such as resistance and capacitance, are monitored by a microdielectrometer. A change in a bond dielectric measurement is indicative of a moisture intrusion in the bond and a corresponding weakening of the structural integrity of the bond. A warning or indication of the bond degradation is provided in response to such changes.

11 Claims, 1 Drawing Sheet

ADHESIVE BOND DEGRADATION MONITOR

BACKGROUND OF THE INVENTION

My invention relates generally to a system for monitoring the structural integrity of a bonded joint and, more specifically, to a system for continuous in-service monitoring of bond degradation corresponding to measured changes in the dielectric properties of the bonding material.

Practitioners in the art of advanced composites have monitored the curing of a composite matrix or laminate part by measuring changes in the dielectric properties of the composite matrix resin such as resistance or capacitance. As the resin cures, changes in the dielectric measurements are used to infer resin viscosity. Active feedback control systems maintain optimal temperature and pressure in autoclave cure cycles in response to changes in resin viscosity.

In these autoclave control systems, small integrated circuit sensors such as the EUMETRIC TM sensor manufactured by Micromet Instruments of Cambridge, Mass. may be attached to the laminate or embedded in it. The sensors are connected by cables in the autoclave to a microdielectrometer, which is a sensitive instrument for measuring small changes in the dielectric properties of the laminate.

Although microdielectrometers and dielectric sensors are well-known in the art, resin-curing monitors are not designed to detect dielectric changes corresponding to decreases in bond strength; they only monitor dielectric changes corresponding to increases in bond strength such as would be experienced during an autoclave curing cycle.

The dielectric properties of the laminate part continue to change long after it is fabricated as it absorbs moisture from the environment. This change, however, is in the reverse direction of that experienced during resin-curing. Moisture absorption results in degradation of structural strength and, eventually, delamination of the part.

Structural members may be bonded using an adhesive resin, which degrades and weakens over time due to moisture absorption in the same manner as in composite laminates. High moisture levels lower the strength of the adhesive, eventually causing failure of the joint.

Critical bonded joints of a structure such as an aircraft are often inaccessible and uninspectable. It is an object of my invention to provide an indication of environmental degradation of bonded joints in structures that are not visually inspectable. It is a further object of my invention to detect not only failures but also trends in the dielectric properties of bonded joints that can be used to estimate the remaining service life of the bonded structure. These problems and deficiencies are clearly felt in the art and are solved by the present invention in the manner described below.

SUMMARY OF THE INVENTION

The present invention comprises a method and apparatus for continuously monitoring changes in the structural strength of a bonding resin during the lifetime of the structure in which the resin is incorporated. The resin may be a bonding resin that joins two adherends or it may be a resin incorporated in a composite laminate part.

In a bonded joint, changes in one or more dielectric properties, such as resistance and capacitance, are monitored by a microdielectrometer. Changes in a bond dielectric measurement are indicative of a moisture intrusion in the bond and a corresponding weakening of the structural integrity of the bond. The present invention monitors the bond for such changes and provides a warning or indication of the extent of the moisture intrusion. Unlike autoclave resin-curing monitors known in the art, the present invention is integrated into the bond and continuously monitors the strength of the bond over the lifetime of the structure. Furthermore, the present invention detects changes corresponding to a decrease in bond strength rather than an increase as detected by resin-curing monitors.

The method is applicable to both metallic and non-metallic adherends and is particularly useful in vehicles such as aircraft. The adherends do not directly contact each other but are separated by the bonding resin. If both adherends are metallic, the terminals of a dielectric measuring device may be directly connected to the adherends, which serve as electrodes. The electrodes may also be permanently embedded in the bonding resin. This method is especially useful where one or both adherends are non-metallic. The electrodes can be discrete electrodes or can be integral to a microcircuit sensor such as the EUMETRIC TM sensor described above.

The measuring device may remain connected to the electrodes for continuous in-service monitoring of the dielectric property or it may be periodically connected to the electrodes at scheduled maintenance intervals.

A moisture intrusion in the bonded joint or laminate lowers the resistance or the capacitance of the adhesive. A warning may be provided when the value of the measured dielectric property reaches a predetermined threshold. In addition, a rate of change in the measured dielectric property may be calculated to extrapolate a corresponding estimate of the remaining service life of the structure.

The foregoing, together with other features and advantages of the present invention, will become more apparent when referring to the following specification, claims, and accompanying drawings.

BRIEF DESCRIPTION OF THE DRAWINGS

For a more complete understanding of my invention, I now refer to the following detailed description of the embodiments illustrated in the accompanying drawings, wherein.

DESCRIPTION OF THE PREFERRED EMBODIMENT(S)

Figure 1:
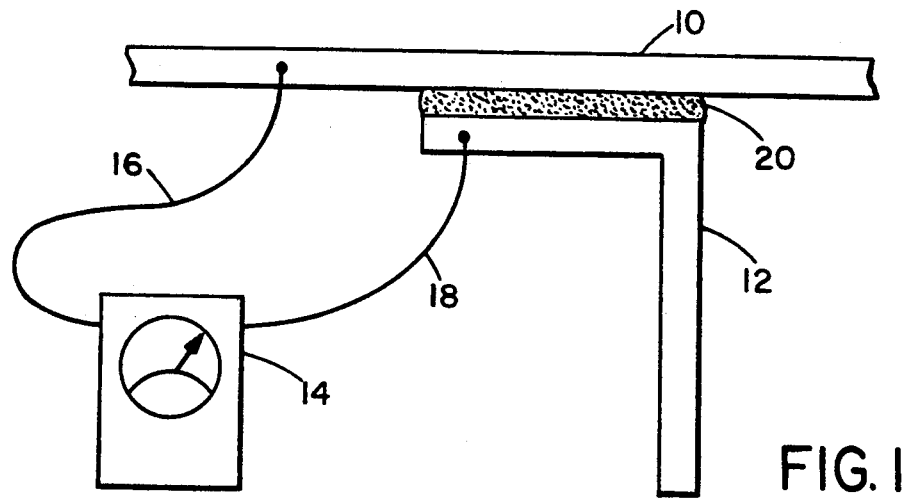
FIG. 1 illustrates a typical joint in which the two adherends are the electrodes.

In FIG. 1, two electrically conductive adherends 10 and 12, which may be structural members of an aircraft or other vehicle, are connected to the terminals of a microdielectrometer 14 using wires 16 and 18. Microdielectrometer 14 monitors one or more dielectric properties in the adhesive resin 20 such as resistance or capacitance. Changes in the dielectric measurement are indicative of moisture intrusion in resin 20 and a corresponding decrease in bond strength. The spacing between adherends 10 and 12 is not critical to the operation of the present invention because it is the change in the dielectric property, rather than the absolute measured value that is indicative of moisture intrusion.

Figure 2:
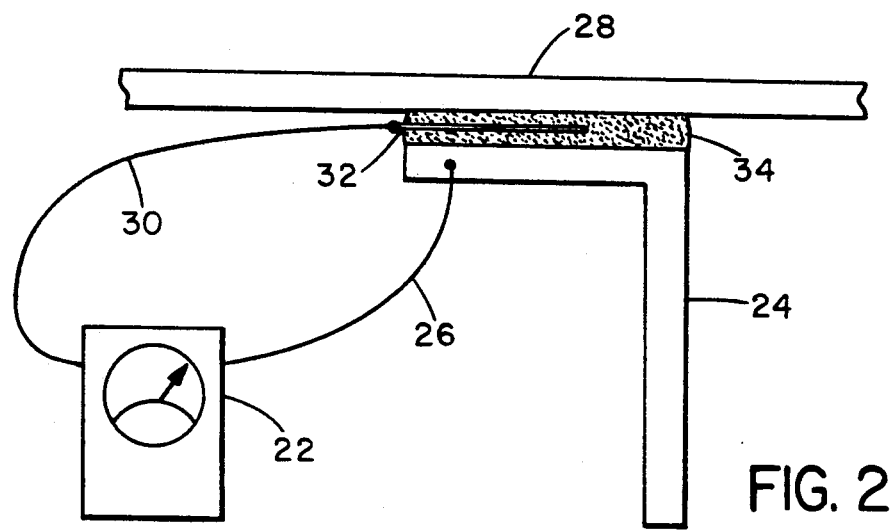
FIG. 2 is a similar view wherein one electrode is embedded in the adhesive.

FIG. 2 shows a second embodiment in which the first terminal of a microdielectrometer 22 is connected to metallic adherend 24 using wire 26 in the same manner as described above. The other adherend 28 may be electrically conductive or nonconductive and does not affect the monitoring system in this embodiment. The second terminal is connected by wire 30 to an electrode 32 embedded in the adhesive resin 34. Electrode 32 is embedded during hardening of the bond ahd is intended to remain permanently embedded throughout the life of the structure. Electrode 32 may be made from any suitable conductive material that is compatible with adhesive resin 34.

Figure 3:
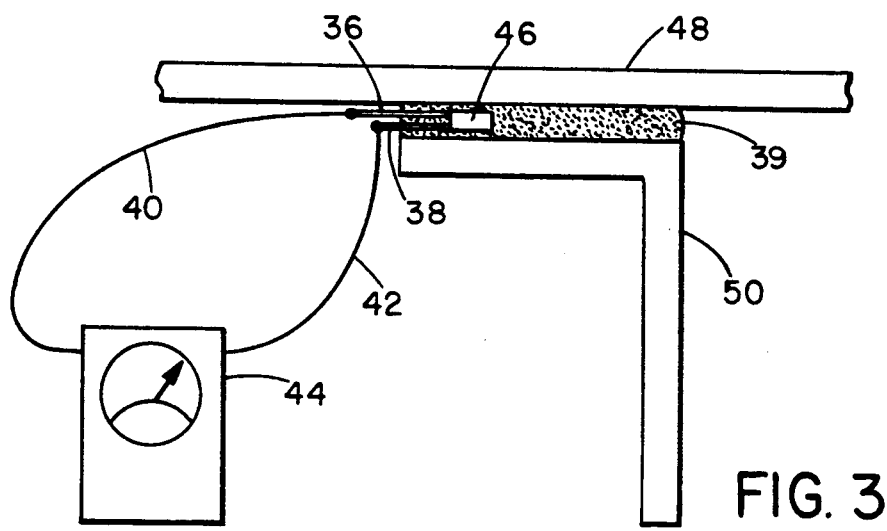
FIG. 3 a similar view wherein both electrodes are embedded in the adhesive.

FIG. 3 shows another embodiment in which both electrodes 36 and 38 are embedded in the adhesive resin 39. Wires 40 and 42 connect electrodes 36 and 38 to the terminals of a microdielectrometer 44. Electrodes 36 and 38 may be discrete electrodes or may be incorporated in a microcircuit sensor 46. The EUMETRIC TM sensor is extremely small, measuring 0.1 inches by 0.2 inches and can be easily embedded in bonded joints during fabrication. Such microcircuit sensors are preferred over discrete electrodes because they provide high sensitivity and resistance to noise in an extremely small package. Adherends 48 and 50 may be made of any suitable material in this embodiment.

In each embodiment described above, the microdielectrometer may provide a warning when the bond degradation exceeds a predetermined threshold. In addition, it may predict the remaining service life of the structure by calculating a rate of change of the measured dielectric property. This rate of change is indicative of the rate of moisture intrusion into the bond. The threshold at which moisture content becomes severe enough to threaten the integrity of the bond may be determined empirically. The current moisture content is then extrapolated forward in time to predict the remaining service life of the bond.

Although only one bond is monitored in each embodiment above, it is understood that any number of bonds may be monitored by connecting a plurality of electrodes or sensors in series or parallel with one another. In addition, multiplexing circuitry may be provided to enable a single microdielectrometer to monitor a plurality of sensors or electrode pairs.

Obviously, other embodiments and modifications of the present invention will occur readily to those of ordinary skill in the art in view of these teachings. Therefore, this invention is to be limited only by the following claims, which include all such other embodiments and modifications when viewed in conjunction with the above specification and accompanying drawings.

I claim:

1. A method for monitoring the degradation of a joint having two adherends bonded with an adhesive therebetween, comprising the steps of:
    measuring a change in a dielectric property of said adhesive over a period of time when said adherends remain in an unchanging physical orientation with repsect to each other; and
    providing an indication of degradation of said joint corresponding to said change in said measured dielectric property.

2. A method for monitoring the degradation of a joint as described in claim 1, at least one said adherend being electrically conductive, further comprising, before said measuring step, the step of electrically connecting a microdielectrometer to said electrically conductive adherend.

3. A method for monitoring the degradation of a joint as described in claim 2, further comprising the step of providing a warning when said degradation exceeds a predetermined threshold.

4. A method for monitoring the degradation of a joint as described in claim 2, further comprising the steps of:
    calculating a rate of change of said degradation; and
    extrapolating an estimate of time remaining until said degradation exceeds a predetermined threshold.

5. A method for monitoring the degradation of a joint as described in claim 1, further comprising, before said measuring step, the steps of:
    embedding an electrode in said adhesive; and
    electrically connecting a microdielectrometer to said electrode.

6. A method for monitoring the degradation of a joint as described in claim 5, further comprising the step of:
    providing a warning if said degradation exceeds a predetermined threshold.

7. A method for monitoring the degradation of a joint as described in claim 5, further comprising the steps of:
    calculating a rate of change of said degradation; and
    extrapolating an estimate of time remaining until said degradation exceeds a predetermined threshold.

8. A method for monitoring the degradation of a joint as described in claim 1, further comprising, before said measuring step, the steps of:
    embedding a microcircuit sensor in said adhesive, said microcircuit sensor not contacting either of said adherends; and
    electrically connecting a microdielectrometer to said sensor.

9. A method for monitoring the degradation of a joint as described in claim 8, further comprising the step of:
    providing a warning if said degradation exceeds a predetermined threshold.

10. A method for monitoring the degradation of a joint as described in claim 8, further comprising the steps of:
    calculating a rate of change of said degradation; and
    extrapolating an estimate of time remaining until said degradation exceeds a predetermined threshold.

11. An apparatus for monitoring the degradation of a joint between two adherends bonded with an adhesive therebetween, comprising:
    a microcircuit sensor embedded in said adhesive, said microsircuit sensor not in contact with either of said adherends;
    a microdielectrometer for measuring change in a dielectric property of said adhesive over a period of time when said adherends remain in an unchanging physical orientation with respect to each other, said change in a dielectric property corresponding to a decrease in joint strength, said microdielectrometer electrically connected to said embedded microcircuit sensor.

* * * * *